United States Patent [19]

Blinka et al.

[11] Patent Number: 5,583,047
[45] Date of Patent: Dec. 10, 1996

[54] METHOD OF DETECTING THE PERMEABILITY OF AN OBJECT TO OXYGEN

[75] Inventors: Thomas A. Blinka, Columbia; Christopher Bull, Bethesda, both of Md.; Charles R. Barmore, Moore, S.C.; Drew V. Speer, Columbia, Md.

[73] Assignee: W. R. Grace & Co.-Conn., New York, N.Y.

[21] Appl. No.: 231,411

[22] Filed: Apr. 22, 1994

Related U.S. Application Data

[63] Continuation-in-part of Ser. No. 988,511, Dec. 10, 1992, Pat. No. 5,316,949.
[51] Int. Cl.$^6$ ..................................................... G01N 31/00
[52] U.S. Cl. ................... 436/5; 436/1; 436/127; 436/138; 436/172; 436/904; 422/56; 422/86
[58] Field of Search ..................... 206/807, 824; 422/56, 86; 436/1, 3, 5, 14, 136, 138, 172, 904, 905

[56] References Cited

U.S. PATENT DOCUMENTS

| | | | |
|---|---|---|---|
| 3,725,658 | 4/1973 | Stanley et al. | 250/71 |
| 3,768,976 | 10/1973 | Hu et al. | 23/254 R |
| 4,023,934 | 5/1977 | Spinner et al. | 23/254 R |
| 4,169,811 | 10/1979 | Yoshikawa et al. | 252/408 |
| 4,349,509 | 9/1982 | Yoshikawa et al. | 422/56 X |
| 4,478,792 | 10/1984 | McConnaughfy et al. | 422/86 |
| 4,526,752 | 7/1985 | Perlman et al. | 422/56 |
| 4,657,736 | 4/1987 | Marsoner et al. | 422/56 |
| 4,659,674 | 4/1987 | Bauman et al. | 436/5 |
| 4,810,655 | 3/1989 | Khalil et al. | 436/136 |
| 5,096,813 | 3/1992 | Krumhar et al. | 422/56 |
| 5,104,811 | 4/1992 | Berger et al. | 422/56 |
| 5,107,696 | 4/1992 | Mayer et al. | 73/38 |
| 5,155,046 | 1/1992 | Hui et al. | 436/136 |
| 5,211,875 | 5/1993 | Speer et al. | 252/188.28 |
| 5,316,949 | 5/1994 | Bull et al. | 436/5 |

FOREIGN PATENT DOCUMENTS

| | | |
|---|---|---|
| 524021 | 1/1993 | European Pat. Off. . |
| 61-144568 | 7/1986 | Japan . |
| 62-12853 | 1/1987 | Japan . |
| 2132348 | 12/1983 | United Kingdom . |

OTHER PUBLICATIONS

"Fluorometric Analysis of Riboflavin and Its Coenzymes"; Jacek Koziol; Methods in Enzymology, vol. XVIII, Vitamins and Coenzymes 1971; pp. 253–285.

"Photochemistry of Flavins"; G. R. Penzer and G. K. Radda; Methods in Enzymology vol. XVIII, Vitamins and Coenzymes 1971; Part B, pp. 479–495.

Fisher Scientific Ctalog 1988, p. SDS 261C.

M. Koizumi et al. *Bull. Chem. Soc. Japan* 1964, 37, 108–117.

A. V. Karyakin et al. *Zh. Fiz. Khim.* 1962, 36, 2286–2287.

A. V. Karyakin et al. *Chem. Abstr.* 1963, 58, 5159c.

K. L. Arvan et al., *Chem. Abstr.* 1964, 60, 8815b.

M. Koizumi et al. *Chem. Abstr.* 1964, 60, 10096f.

C. Kemal et al. *J. Am. Chem. Soc.* 1977, 99, 7272–7286.

J. Cantet et al. *Angl. Chem.* 1990, 62, 1502–1506.

C. Franco et al. *Talanta* 1990, 37, 905–909.

*Primary Examiner*—Arlen Soderquist
*Attorney, Agent, or Firm*—Valerie E. Looper

[57] ABSTRACT

A method of detecting the permeability of an article to oxygen is disclosed. A fluorescent redox indicator, preferably riboflavin, is dispersed in a carrier and placed on an impermeable substrate. The article to be measured is placed adjacent to the carrier. Residual oxygen is removed, the redox indicator is photoreduced, the article and carrier are exposed to oxygen, and the indicator is exposed to UV light.

9 Claims, 15 Drawing Sheets

METHOD OF DETECTING THE PERMEABILITY OF AN OBJECT TO OXYGEN

This application is a continuation-in-part of U.S. Ser. No. 07/988,511, filed Dec. 10, 1992, now U.S. Pat. No. 5,316,949, which is incorporated by reference.

FIELD OF THE INVENTION

This application relates to a method of detecting the oxygen permeability of an article and various improved ways of implementing that method. This method allows the detection of flaws in an oxygen barrier such as pinholes and cracks, as well as the overall permeability over time. Further, this method can be re-used several times to show whether the oxygen barrier's characteristics change over time. The method is easy to set up and use, and provides quick results. Compared to the available technology, this method is far cheaper, and yields an order of magnitude increase in sensitivity. Unlike available technology, this method can spatially resolve the permeability of an object, i.e., detect streaks, cracks, pinholes and other features. Also, this method more closely correlates with the real-world use for which it was originally developed, to test a food wrap, since it uses a food simulant and ambient temperature, pressure, humidity and gas mixtures for test conditions. In particular, this application relates to improved fluorescent oxygen indicating formulations which allow easier sample preparation and greater indicator stability.

BACKGROUND OF THE INVENTION

It has been found that polymeric materials can be drawn into thin, transparent films. When this is done, however, it is difficult to tell whether the film has been properly made, or whether it has flaws, especially if the film has multiple layers. Many critical flaws are not visible. Hand calibration of thickness is not feasible. The standard analytical instrument for measuring oxygen permeability, as described in U.S. Pat. No. 5,107,696, can only detect average permeability over an area typically five square inches.

Various methods of measuring the presence of oxygen are known for use in various systems. Liquid systems are discussed in U.S. Pat. No. 4,659,674 issued to Bauman et al., Apr. 21, 1987, which discloses an ion-specific electrode. The possibility of determining oxygen permeation via pH change is discussed but only overall permeability is disclosed, and surface flaws such as pinholes in a barrier could not be detected.

The amount of oxygen in a gaseous stream has also been measured. For example, U.S. Pat. No. 3,725,658, issued to Stanley et al., Apr. 3, 1973, relates to a medical oxygen analyzer. It discloses an apparatus and method for continuously detecting rapid changes in the oxygen content of a gas stream; that is, a total response time of not more than 0.1 seconds per measurement. The reference relies on the use of a fluorescent material such as pyrene, coronene and p-terphenyl whose fluorescence is partially quenched by the presence of oxygen. Elaborate mechanical support is required. There is no spatial resolution of oxygen flow.

Oxygen detectors have been used in packaging. U.S. Pat. No. 4,526,752, issued to Perlman, Jul. 2, 1985, relates to a tamper-resistant package. A dye, such as methylene blue, which is colorless in the reduced state and becomes colored upon exposure to oxygen is dissolved in water along with a volatile reducing agent. The reducing agent is removed, along with the water, preferably under vacuum, and the package is sealed. If the package is broken, the dye will become colored upon exposure to air. The change in color of the package is irreversible.

Another type of oxygen detector is used in U.S. Pat. No. 3,768,976, issued to Hu et al. Oct. 30, 1973, which relates to a temperature-time indicator for food packaging. The indicator is a film package that contains an aqueous solution of a redox dye such as sodium anthraquinone beta-sulfonate. The dye in its reduced state is dark red and obscures a warning message. As oxygen permeates into the package in an amount which is dependent on temperature and time, the dye fades and the warning message is revealed. This system is not reversible, and spatial resolution of the rate of oxygen permeation is not disclosed or discussed.

Similarly, U.S. Pat. No. 4,169,811, issued to Yoshikawa Oct. 2, 1979 discloses an oxygen indicator which is a dye, a base, and a reducing agent. The dye has one color in an anaerobic environment and another color in an aerobic environment. These dyes are derivatives of methylene blue. It is disclosed that these dyes require the presence of water or an alcohol in order to function. The reducing agents are disclosed to be saccharides, dithionites and ferrous compounds. The oxygen sensitivity is disclosed to be as low as 0.1% [column 6, line 65].

A probe is disclosed in U. K. Patent Application 2132348A, which relates to the use of platinum group metal complexes which luminesce when excited by visible or UV light, and which are quenched by oxygen and other materials. A sensor, which incorporates the metal complex in a carrier, which must be permeable to oxygen and relatively impermeable to other quenchers is exposed to the environment and oxygen permeates the carrier and partially quenches the fluorescence of the metal complex. The quenching-related decrease in intensity or lifetime of luminescence is measured and correlated to the presence of oxygen. The precision and accuracy is about 2 percent. Spatial resolution of oxygen permeability is not disclosed. The use of a sensor akin to pH paper is discussed, which is said to yield only semi-quantitative or qualitative oxygen monitoring (Col. 8, lines 116–126).

The difficulty with many indicators is that they are not physically compatible with the most likely carriers.

U.S. Pat. No. 4,657,736, issued to Marsoner et al. Apr. 14, 1987, addresses this point, disclosing that fluorescent indicators can be reacted with tertiary butyl chloride to render them compatible with silicone polymer carriers to avoid having the indicator crystallize out of the polymer.

What is needed is a method of detecting oxygen transmission through a barrier that is useful for quality control in day-to-day manufacture of polymer sheets and other objects, and for design and development of new oxygen barrier materials. The method should be relatively quick and be both qualitative and quantitative. It should also be activated on demand and capable of detecting manufacturing defects such as streaks and pinholes. Also desirable are methods and devices for automating this method, to improve its cost and convenience of operation.

Although this application is written in terms of a specific end use, one of ordinary skill in the art will readily recognize that it is a general tool for detecting cracks and pinholes wherever oxygen might be used as an indicator. For example, it could be used to detect flaws in sheets of aluminum foil. In that case, oxygen permeability per se might not be the primary interest, if one is interested in the physical integrity of the foil. Similarly, the integrity of opaque or tortuous path type materials such as ceramics could be tested as well.

The inventors have found that a system based on the reaction of a redox indicator can be used to measure oxygen transmission in great physical detail, that is, make an image of a barrier's permeability. This Low Oxygen Transmission Imaging System ("LOTIS") can be used in both qualitative and quantitative modes.

OBJECTS AND ADVANTAGES OF THE INVENTION

It is, therefore, an object of this invention to provide a method and apparatus for detecting the rate of permeation of oxygen through a barrier at various locations.

Another object is to provide as the detecting component for oxygen analysis a stable sheet comprising a redox compound dissolved in a solvent or dispersed in a carrier, which sheet is supported on a substrate and is re-usable.

Yet another object of the invention is to provide indicator formulations that exhibit both improved dye stability and handling characteristics, as well as to provide extrudable formulations. Another object is to provide additional photoreducible indicator dyes.

This invention offers a number of advantages, including the ease and speed with which a spatial representation of the oxygen permeability of an object can be obtained.

A particular advantage of the present invention is that the redox compound and carrier can be stored indefinitely under ambient, that is, oxygenated conditions. Previous systems using chemical reductants and redox dyes had to be prepared and used fresh due to their oxygen reactivity.

The type of redox compound or a mixture of redox compounds can be manipulated to obtain test results in a convenient amount of time.

The use of different types of carriers can result in more stable fluorescent formulations; particular formulations are extrudable and therefore well-adapted to a mechanized test.

DETAILED DESCRIPTION OF THE INVENTION

To use this invention, a redox indicator is dispersed in a carrier, typically along with a photoreducing agent, and placed on a support which is not a potential oxygen source. The object which is being tested is placed next to the indicator to make a sandwich structure or plate. It is preferred that residual oxygen in the carrier and object themselves be removed. This can be conveniently done by flushing with nitrogen, or a vacuum treatment of the plate (or both), followed by photoreduction. To photoreduce the indicator, the plate is exposed to UV light or any ambient fluorescent or incandescent light for an empirically determined period of time. The photoreduced plate is now essentially devoid of fluorescence because the indicator is in a photoreduced state. Examining the plate under UV light will confirm the lack of fluorescence.

In order to measure the permeability of the object to oxygen, the plate is allowed to equilibrate under ambient conditions in the dark for a predetermined time. Then the plate is then exposed to UV light to excite the fluorescence of the oxidized indicator. Areas of relatively low permeability will be dark, while areas of higher permeability will show a brighter fluorescence. The position of streaks, pinholes and surface artifacts can be resolved to a location within an area of 1/16 square inch. It is important to the quantitative practice of this invention that the light used to read the fluorescence of the plate is of such an intensity and duration that it does not cause significant photoreduction.

INDICATOR

A system based on riboflavin as the redox indicator is preferred because

1) Riboflavin exists in two redox states: an oxidized, highly fluorescent state and a reduced, much less fluorescent state. This second state exhibits a weak fluorescence at a different wavelength from the first, which is easily removed with suitable filters.

2) Riboflavin is photoreducible in the presence of a photoreducing agent such as ethylene-diaminetetraacetic acid ("EDTA") or oxalate. "Photochemistry of Flavins" Penzer & Radda, *Methods in Enzymology*, Vol. XVIII, part B, pp. 479–495, Academic Press, NY, (1971). Photoreduction is important in this context because it yields a significant advantage over chemical reduction methods. It should be noted that EDTA does not reduce riboflavin in the absence of light. The plates can be activated upon demand. In addition, once the riboflavin is reduced, there is no excess chemical reductant present. The subsequent reoxidation reaction is known to be quantitative. "Fluorometric Analyses of Riboflavin and Its Coenzymes", Kozoil *Methods in Enzymology*, Vol. XVIII, part B, pp. 253–285:256, Academic Press, NY, (1971).

3) Reduced riboflavin is highly reactive with oxygen to regenerate the oxidized state. Also, in the context of this invention, once the oxygen is reacted, it is trapped and little diffusion occurs. Images which are made using this method are relatively sharp.

4) Riboflavin, (also known as Vitamin B-2) is biocompatible, and so its use does not present environmental concerns.

This system is described in terms of riboflavin because it is a redox indicator particularly suitable for the inventors' purposes.

However, various flavin derivatives and other redox dyes such as the azine, thiazine and oxazine derivatives are also operable, and may be desirable in certain circumstances. For instance, riboflavin oxidizes so quickly that it is not convenient to use riboflavin in the present method to directly determine the oxygen transmission of highly permeable films such as thin polyethylene. One viable approach to measuring the permeability of such films would be to reduce the amount of oxygen in the test gas mixture. This of course would require additional gas delivery and handling apparatus. Another approach would be to use a redox dye that reacts more slowly with oxygen, such as methylene blue. A variation on this technique would be to use two dyes having different oxidation rates. In Example 6, for instance, methylene blue is used in tandem with riboflavin. The riboflavin provides a convenient method of photoreducing (as opposed to chemically reducing) the methylene blue.

Methylene blue is known for being chemically reducible. If it is to be used as an oxygen indicator, it has to be placed in the reduced state and then protected from exposure to oxygen. For accurate detection, the amount of chemical reducing agent would have to precisely match the amount of methylene blue present. In addition, the methylene blue and chemical reducing agent would have to be rapidly mixed and immediately and physically isolated from air. The process is not reversible.

If the riboflavin is added, the methylene blue and riboflavin can be blended and soaked into an indicator strip in an oxidized state, and can be stored under oxygenated conditions. When the operator chooses, the indicator strip and test object are placed together in a test package, residual oxygen is removed, and the test package is exposed to light. Upon exposure to light, the riboflavin will be photoreduced to an entity called leuco-riboflavin, which is a potent chemical reducing agent. The leuco-riboflavin rapidly reduces the methylene blue, thus providing a convenient method of obtaining reduced methylene blue inside a sealed package. The package can then be exposed to ambient conditions in the dark, and the methylene blue can respond to the oxygen which permeates into the indicator strip. Areas of the test object with higher permeabilities will turn blue faster than areas of low permeability.

Close control of the relative amounts of methylene blue and riboflavin is not required, and the test is repeatable. Further, this test method can rely on visible light instead of ultraviolet light, a distinct advantage when a visible light response is desired. This method provides a more convenient time scale of minutes rather than seconds for reoxidation of the indicator dye.

A potential problem with methylene blue is permanent photobleaching, due to instability of the dye. Oxazine dyes such as Nile Blue A and Celestine Blue are more stable than thiazine dyes such as methylene blue. Since any dye with a redox potential less than that of riboflavin could be conveniently photoreduced by it, a riboflavin/oxazine indicator might be especially advantageous when repeated tests are desired.

One of ordinary skill in the art will readily recognize that other redox systems are usable, particularly for non-food applications.

CARRIER

The carrier is preferably some easy-to-handle gel such as gelatin, cornstarch, agar, etc. One of ordinary skill in the art will recognize that any solid or liquid in which the redox indicator is dispersible, and which has desirable handling properties, can be used.

A particularly desirable carrier would be one which is extrudable. In theory, any extrudable thermoplastic in which the redox indicator is dispersible is usable in the present invention. A thermoplastic has an added advantage over a carrier such as gelatin because thermoplastic is not so easily subject to attack by microorganisms. Such materials include polymers and copolymers of ethylene oxide, vinyl alcohol, vinyl acetate acrylic acid, and methacrylic acid. High molecular weight polyethylene oxide is commercially available as the Polyox™ series of polymers from Union Carbide Corp., Danbury, Conn. and is preferred.

The support is any sheet of material which is less permeable to oxygen than the test article, does not fluoresce, and which has appropriate handling properties for the application. Appropriate supports could be glass or plastic plates, or flexible films.

The photoreducing agent can be any organic aliphatic amine or amino acid that will function as an electron source, i.e., is capable of being oxidized. Of these, ethylenediaminetetraacetic acid, triethanolamine and triethylamine may be mentioned. Sugars will work, as well as riboflavin itself and various flavin derivatives, and also alcohols.

Accelerators can also be added, of which a buffer such as trisodium citrate dihydrate is an example. In this context, an accelerator will speed up the photoreduction step, resulting in a shorter testing time. Up to about 3% by weight can be used.

Scattering agents can also be used to increase the fluorescent response. Any particulate or fibrous material can be used. Titanium dioxide and finely ground silica gel particles or paper fiber can be used. In addition, other additives such as antifoam and mold inhibitors may be added.

In one embodiment of the present invention, a piece of absorbent paper is saturated with a warm gelatin mixture:

| Ingredient | % by weight |
| --- | --- |
| Riboflavin | 0.01 |
| Gelatin | 7.0 |
| Disodium EDTA | 0.7 |

The indicator paper is then cooled and the gelatin allowed to congeal. The indicator paper may be stored at this point for an indefinite period of time, preferably under low light conditions, with care to avoid drying out of the gelatin. The indicator paper is then placed on a glass plate which has a larger surface area than the indicator paper. A bead of stopcock grease is run around the border of the indicator paper and the test film is smoothed over both the paper and bead. The plate is placed in a bag having a high barrier to oxygen and a vacuum drawn. This step serves the dual purpose of withdrawing as much oxygen as possible from the plate (support, indicator and test film) and also forces the stopcock grease to form a seal between the test film and support. After vacuum treatment, the plates are stackable and easy to handle.

The plate is then photoreduced by exposure to strong UV or visible light while still in the vacuum bag. When the test is started, the bag is removed and the plate is exposed to ambient, low light conditions. After a given period of time, the plate is again exposed briefly to UV light. Areas of relatively high permeability are seen as bright spots against a dark background. If desired, quantitative resolution of oxygen permeability can be had using known fluorescent detection methods.

One of ordinary skill in the art will readily recognize that this test is adaptable to a variety of materials and conditions. For example, the test method as written is convenient for use with transparent films having an oxygen transmission rate of about 0.001–200 cc/m$^2$ (atm.day). Objects with higher oxygen permeability can be tested using a lower concentration of oxygen in the test gas mix, or using a different indicator. Objects with very low oxygen permeability could be tested without ever removing the vacuum bag. The films described in this application are transparent, and fluorescence readings were taken from the sample side of the plates. Non-transparent objects (such as printed bags or aluminum foil) can also be tested using a transparent support. In that case, fluorescence readings are taken from the support side of the plate.

Figure 1:
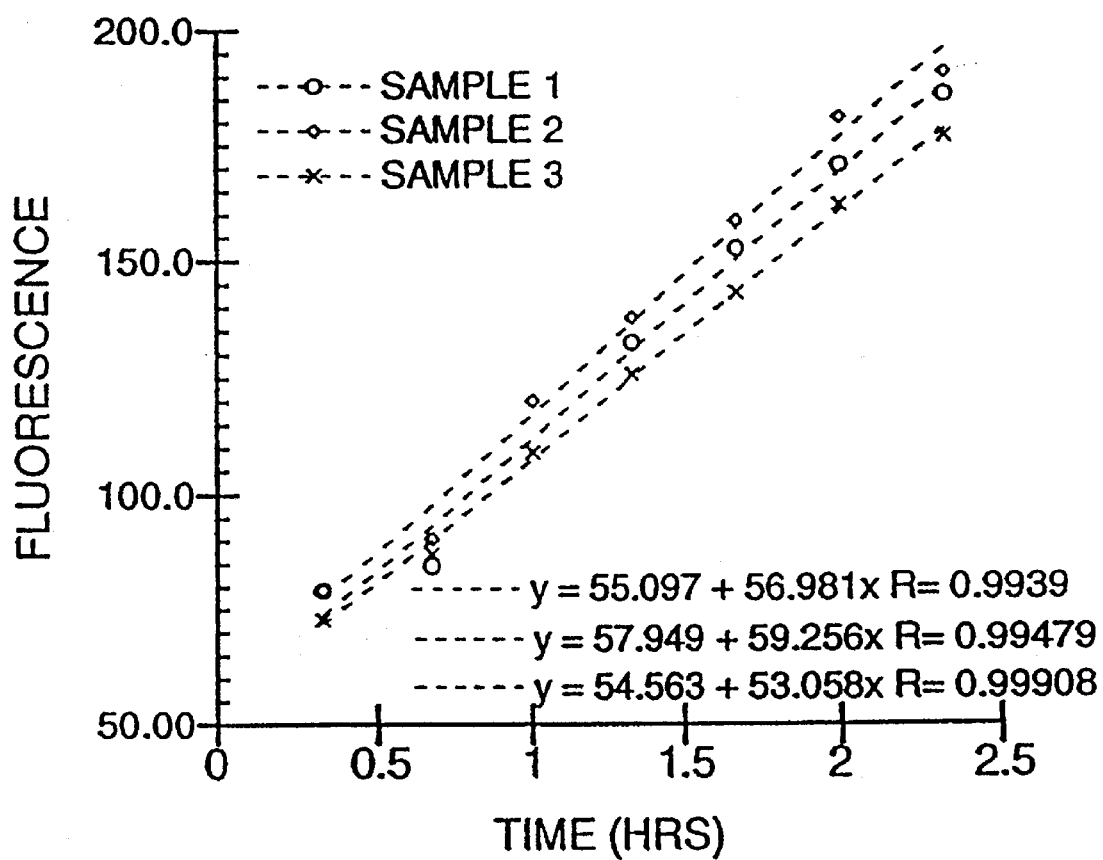
FIGS. 1–4 are graphs of the fluorescence levels for film samples A–D.
Figure 2:
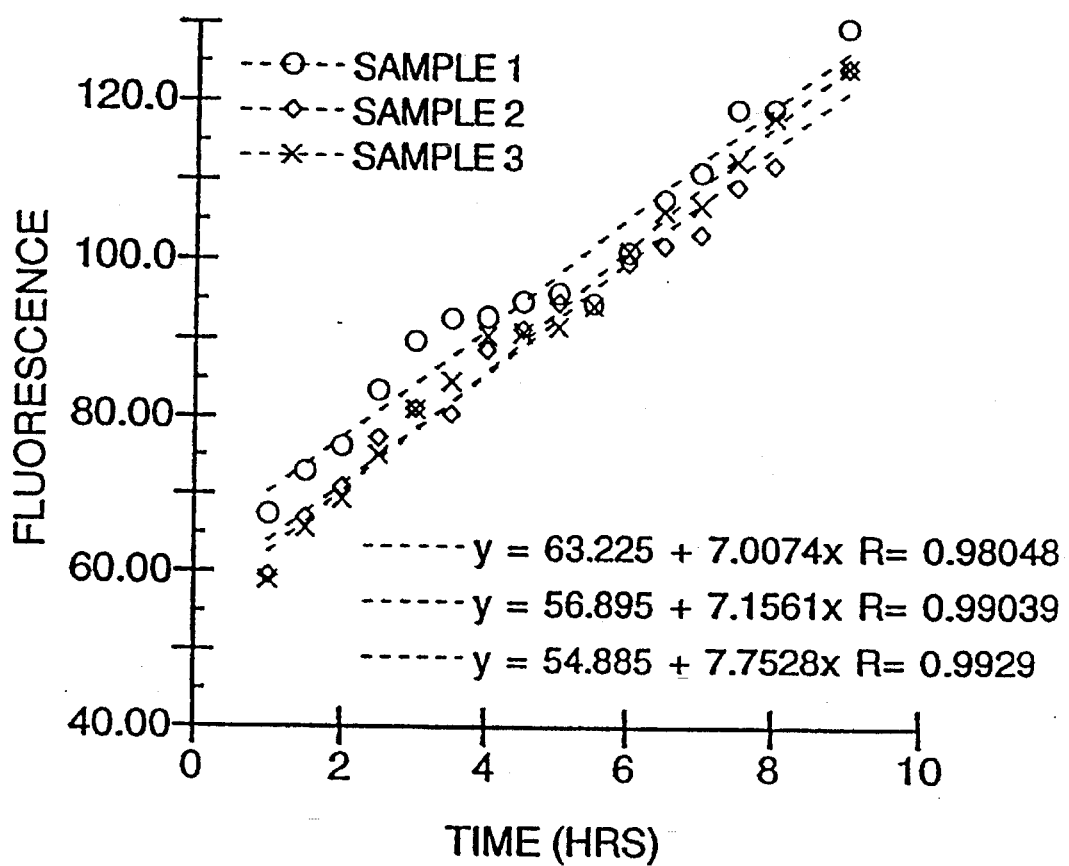
Figure 3:
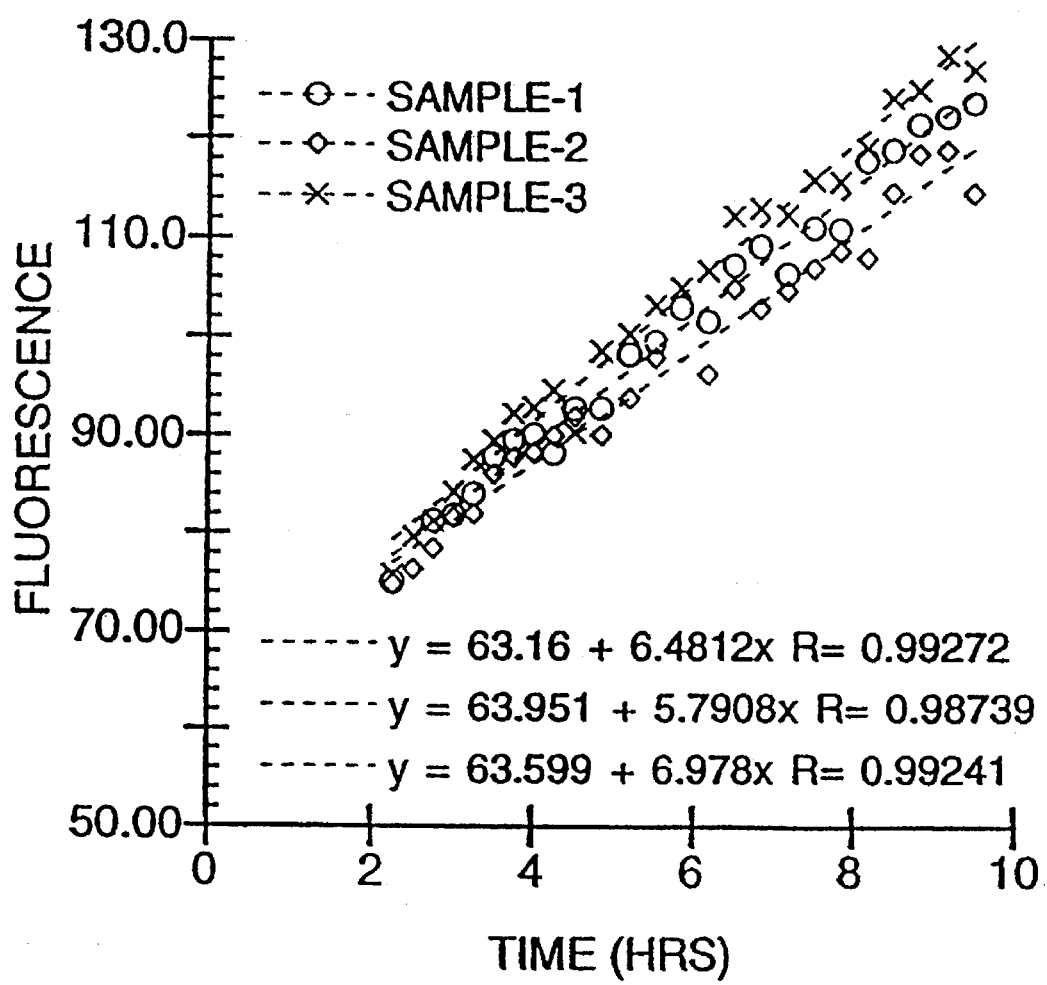
Figure 4:
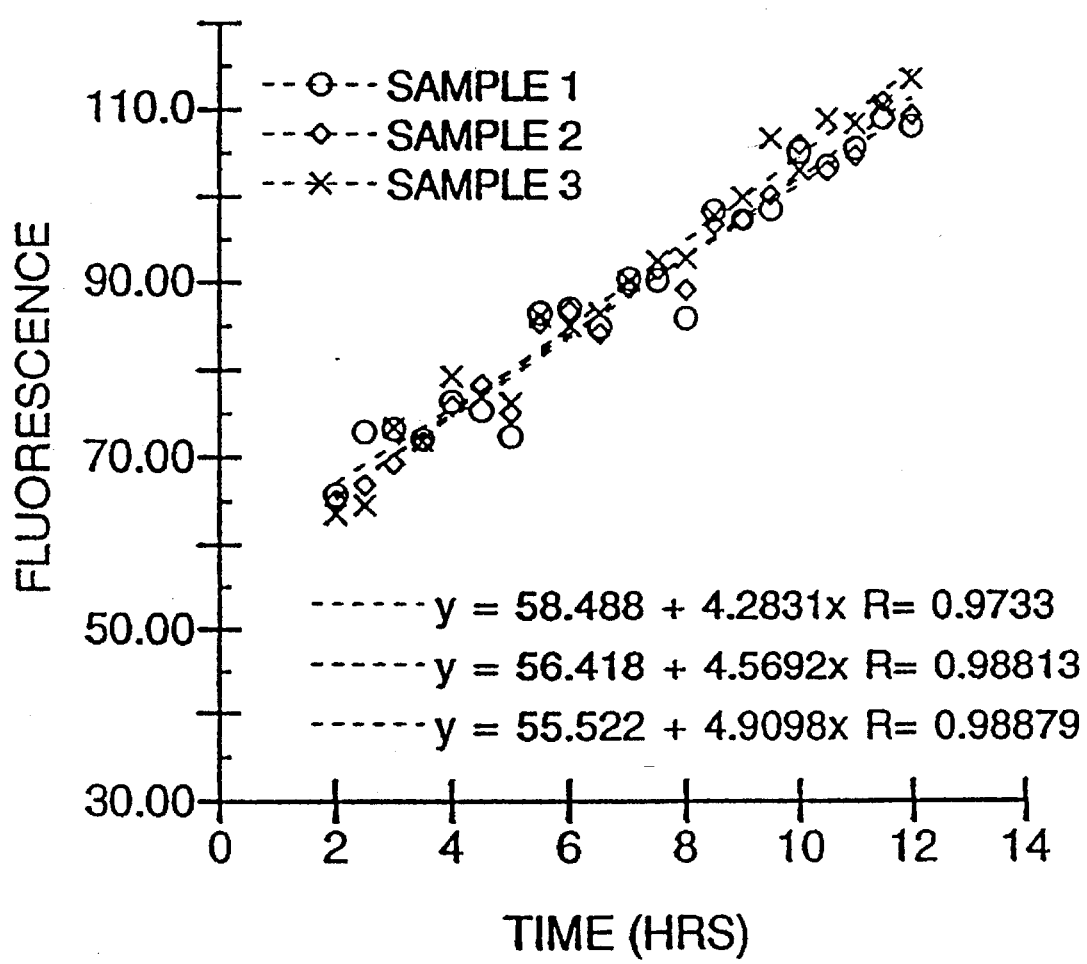

The following examples illustrate the use of the invention described herein without limiting its scope or the scope of the claims which follow.

EXAMPLE 1

Comparison of LOTIS and Standard Instrument Data

Raw values for oxygen transmission of the same 50 cm$^2$ areas of four samples of different oxygen barrier films were compared using the present invention (LOTIS) and an Ox-Trans™ 1000 unit from Modern Controls, Inc., Minneapolis, Minn.

A gel was made incorporating an oxidation-reduction system with riboflavin as the oxidizable substrate and sodium EDTA as a reducing aid during the photo-reduction process. The recipe for the gel was as follows:

| | |
|---|---|
| Gelatin | 7 grams/100 mls water |
| Disodium EDTA | 300 milligrams/100 mls water |
| Riboflavin | 20 milligrams/100 mls water |
| Antifoam B | 1 drop (to prevent foaming of solution) |

The EDTA was dissolved in the water first, using a magnetic stirrer and slight heat. After the EDTA was completely dissolved, the gelatin was added, leaving the beaker on slight (low) heat. When the gelatin was fully hydrated and dissolved, the riboflavin was added. The mixture was stirred until the riboflavin appeared well mixed, and then poured into a shallow, slightly heated double boiler apparatus. Pieces of absorbent paper 3MM CHR™ chromatographic paper, non-fluorescent, from Scientific Products, Charlotte, N.C., were placed in the double boiler and allowed to soak up the gel. The object was to keep the gel warm so that it will not set before the paper medium has been impregnated, but not to burn or scorch the gel. After the absorbent paper had been impregnated with the warm gel, the excess gel was gently removed from the medium using a roller, and the impregnated paper was placed in a refrigerator to allow the gel to set.

The indicator strips were dampened on both sides with an atomizer and affixed to glass plates. A bead of stopcock (vacuum) grease was run around the edge of the strip. The test material was smoothed over both the indicator strip and the stopcock grease. A border of double-sided tape was run around the very outer edge of the glass plate to aid in sealing the test material to prevent oxygen leakage. The prepared plates were vacuum packaged in a plastic pouch which has a high barrier to oxygen transmission and photoreduced under fluorescent lights. The pouch was removed and a picture was taken to record the initial state of fluorescence of each plate. The exposed plates were placed in a dark cabinet for protection from light while they oxidized. Subsequent pictures of the oxidizing (and fluorescing) plates were taken at various time intervals and were digitally recorded using a computer and appropriate software. It should be appreciated that the light levels used to record the fluorescence were much less than those necessary to cause photoreduction.

When the plates were sufficiently fluorescent—after several (8 or more) hours of exposure or after "raw" fluorescence reading of over 200 analog-to-digital conversion units was reached—a circle of approximately 3.15 inches in diameter (approximately 7.8 sq. in. or 50 sq. cm) was drawn on the test material to mark the exact area for evaluating oxygen transmission by both the LOTIS method and the Ox-Trans unit. The mean pixel count (fluorescence level) of the test area at each time interval was determined using the appropriate software, and was repeated for all materials tested. These pixel counts were plotted on a graph versus time. The data in the "linear" portion of the graph were used to determine a "best-fit line" and linear regression equation shown in FIGS. 1–4. The slope of the regression equation= "b" when the equation is in the form Y=a+bx should be proportional to the oxygen transmission rate of the material.

The oxygen transmission rates of the test areas were determined using an Ox-Trans 1000™ unit according to standard procedure.

An initial period of non-linearity that was typical of each given type of material was observed. Without being held to any particular theory, it is believed this period represents the set-up of steady-state oxygen permeation through the film. Once the system had equilibrated, however, the fluorescence increased linearly with time, as expected.

The data for each sample is listed in Table 1 below. The average rate of transmission over a period of time for each sample as found by LOTIS method was compared to the single value per item obtained by the standard instrument. The LOTIS units are reported as fluorescent units/hr. The raw data had to be calibrated to correct for the camera and lens sensitivity. The system is less sensitive around the edges. Consequently, the correction can be made either physically or mathematically using a dome-shaped function that is characteristic for a given lens. Correlation among individual samples for each type of material was good.

Figure 5:
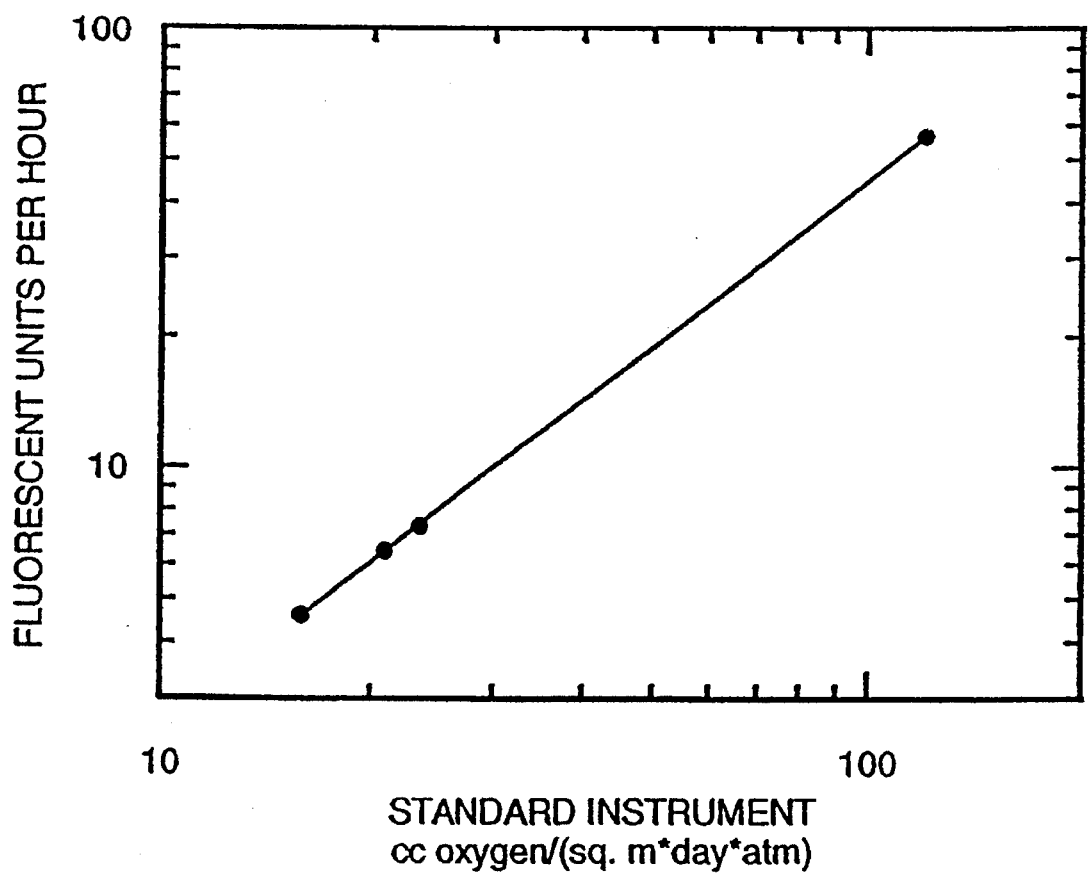
FIG. 5 is a comparison of LOTIS and OTC data in fluorescent units per hour.

The four different materials each had different overall rates of oxygen transmission. When these overall rates are compared to the instrumental data using a log plot, a linear result with a high correlation coefficient (R-0.99997) was reported (See FIG. 5).

In sum, these experiments show that correlation between the LOTIS system and the standard instrument may be close enough to use for quantitative applications.

TABLE 1

| Sample | Standard Instrument (cc/m$^2$/24 hours @ 73° and 0% RH) | LOTIS FLuorescent Units*/ hour |
|---|---|---|
| A-1 | 119.3 | 57.0 |
| -2 | 122.3 | 59.3 |
| -3 | 120.4 | 53.1 |
| B-1 | 23.3 | 7.0 |
| -2 | 22.7 | 7.2 |

TABLE 1-continued

| Sample | Standard Instrument (cc/m²/24 hours @ 73° and 0% RH) | LOTIS FLuorescent Units*/ hour |
|---|---|---|
| -3 | 24.5 | 7.8 |
| C-1 | 20.4 | 6.5 |
| -2 | 20.8 | 5.8 |
| -3 | 21.6 | 7.0 |
| D-1 | 15.9 | 4.3 |
| -2 | 15.7 | 4.6 |
| -3 | 14.9 | 4.9 |

*Corrected for camera lens sensitivity calibrated dome-shaped function (in text).

EXAMPLE 2

Detection of Damage

Figure 6:
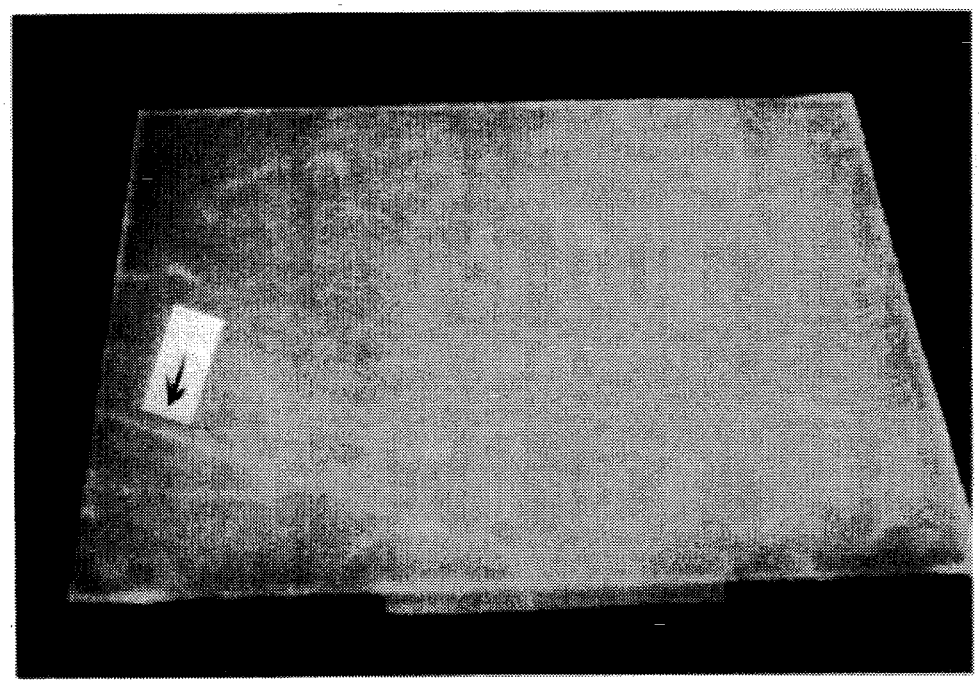
FIG. 6 is a photograph of a damaged oxygen barrier film.

FIG. 6 is a photograph of an experimental 1 mil polyester film (E) coated with 1000 Angstroms (0.1 micron) of silica, which serves as an oxygen barrier. This film was deliberately creased in order to disrupt the silica coating. The fluorescing line marked by the arrow corresponded to the location of the crease.

EXAMPLE 3

Detection of a Manufacturing Flaw

Figure 7:
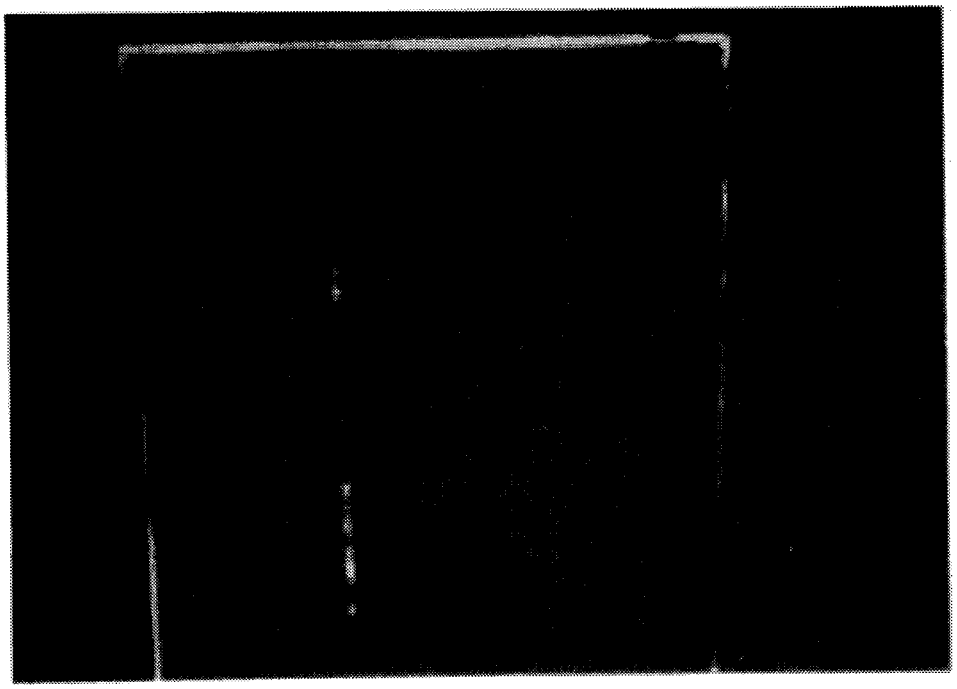
FIG. 7 is a photograph of a film sample with a manufacturing flaw.
Figure 8:
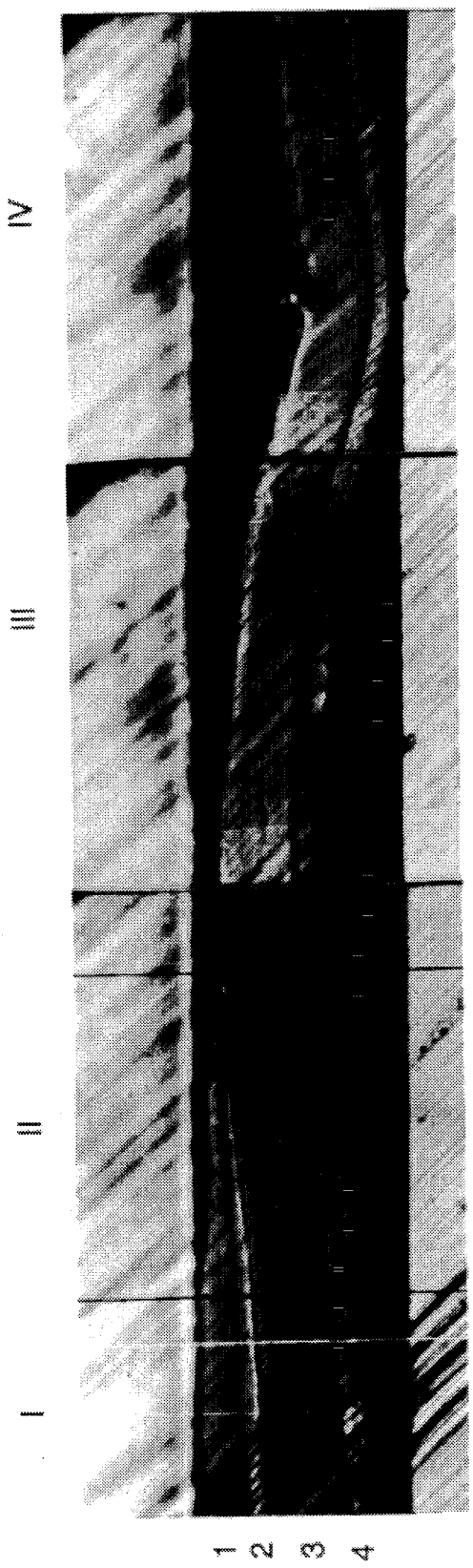
FIG. 8 is a photograph of a microscopic cross section of the film of FIG. 7 in the region of the flaw.

A sample of a four-layer oxygen barrier film that showed a highly fluorescent streak when tested using the LOTIS system was subjected to microscopic examination. FIG. 7 is a photograph of the fluorescing plate. FIG. 8 is a photograph of a microscopic cross section of the same material in the region of the fluorescing streak. Zone 1 shows the intact four layer structure about 1.7 mils thick from the non-fluorescent area marked "NF" on FIG. 7. The layers were as follows:

1 - Sealant—poly(ethylene vinyl acetate)/polyolefin blend, nominally 0.3 mils

2 - Oxygen Barrier—poly(vinylidene dichloride methyl acrylate), nominally 0.16 mils 3 - Core—poly(ethylene vinyl acetate), 1.04 mils 4 - Outer—acrylate copolymer, 0.47 mils.

Zone II shows a thinning of layers 1 and 2. Zone III shows the absence of layers 1 and 2. Zone III is taken from the highly fluorescent area marked "F" on FIG. 6.

This technique can also be useful to detect extrusion variations of the oxygen barrier materials that are not, strictly speaking, flaws in a given material. The technique can be used as a tool to analyze variations in layer thickness, uniformity of blending and peculiarities of starting and stopping of extrusion. When the barrier is deposited on a surface, deposition patterns can be detected, to the extent they are related to oxygen permeability.

EXAMPLE 4

Additional Oxgen Indicating Dyes

Two oxygen-indicating formulations were prepared as follows: a 2% agar solution was prepared in a pH 8 "Tris" tromethamine, or 2-amino-2-hydroxymethyl-1,3-propanediol, buffered water. The mixture was heated to boiling briefly, until the agar dissolved, and cooled to 35°–40° C. Indicator dye was added to make a 0.4 mM solution, and triethanolamine was added to make a 0.8 mM solution. The mixture was stirred until the ingredients were dissolved. Indicating paper was prepared by dipping Whatman 3 MM CHR in the warm solution (35°–40° C.), draining excess solution, then cooling to allow the agar to "set". In one formulation, riboflavin was the indicator dye, and in the other formulation, lumichrome (7,8 dimethyl alloxazine, a flayin dye available from Aldrich Chemical Co., Milwaukee, Wisc.) was the indicator dye.

The coated paper was placed on a glass plate. The glass plate, together with the coated paper, was vacuum sealed in a heavy duty oxygen barrier bag (Cryovac® B540 barrier bag, approximate oxygen transmission rate 20 cc $O_2/m^2$.day.atm available from the Cryovac Division of W. R. Grace & Co.-Conn., Duncan, S.C.).

The samples were then photoreduced periodically for 2 hours on a GB11-36 light table available from Instruments for Research and Industry, Inc. ("I²R™ light table").

Figure 9:
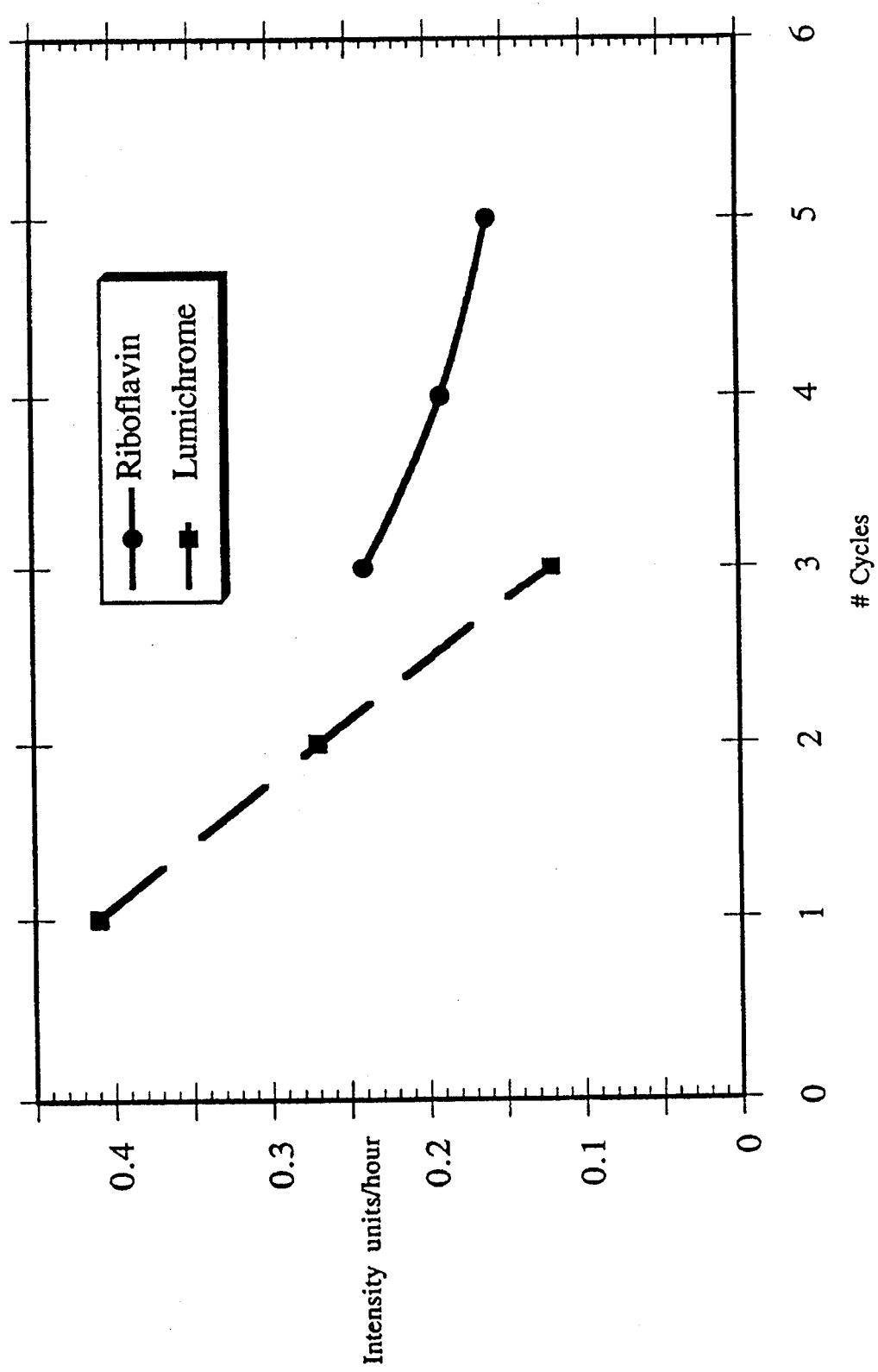
FIG. 9 is a plot of the change in fluorescent intensity of formulations containing lumichrome and riboflavin indicator dyes over several redox cycles.

Two parameters were measured: The initial fluorescence intensity immediately after photoreduction, and the rate of fluorescence increase over time. The fluorescence intensity after 2 hours of photoreduction measures the photoreduction kinetics of the oxygen indicating formulation: formulations which reduce rapidly will have low intensity values, while slower photoreduction rates result in higher values (the intensity scale ranges from 0, no fluorescence, to 255 at maximum fluorescence). The slope of the fluorescence versus time curve measures the sensitivity of the reduced indicator to oxygen permeating through the barrier bag film, which is typically assumed to be constant over time. The results, plotted as a function of the number of complete photoreduction-reoxidation cycles of the formulations are shown in FIG. 9.

Figure 10:
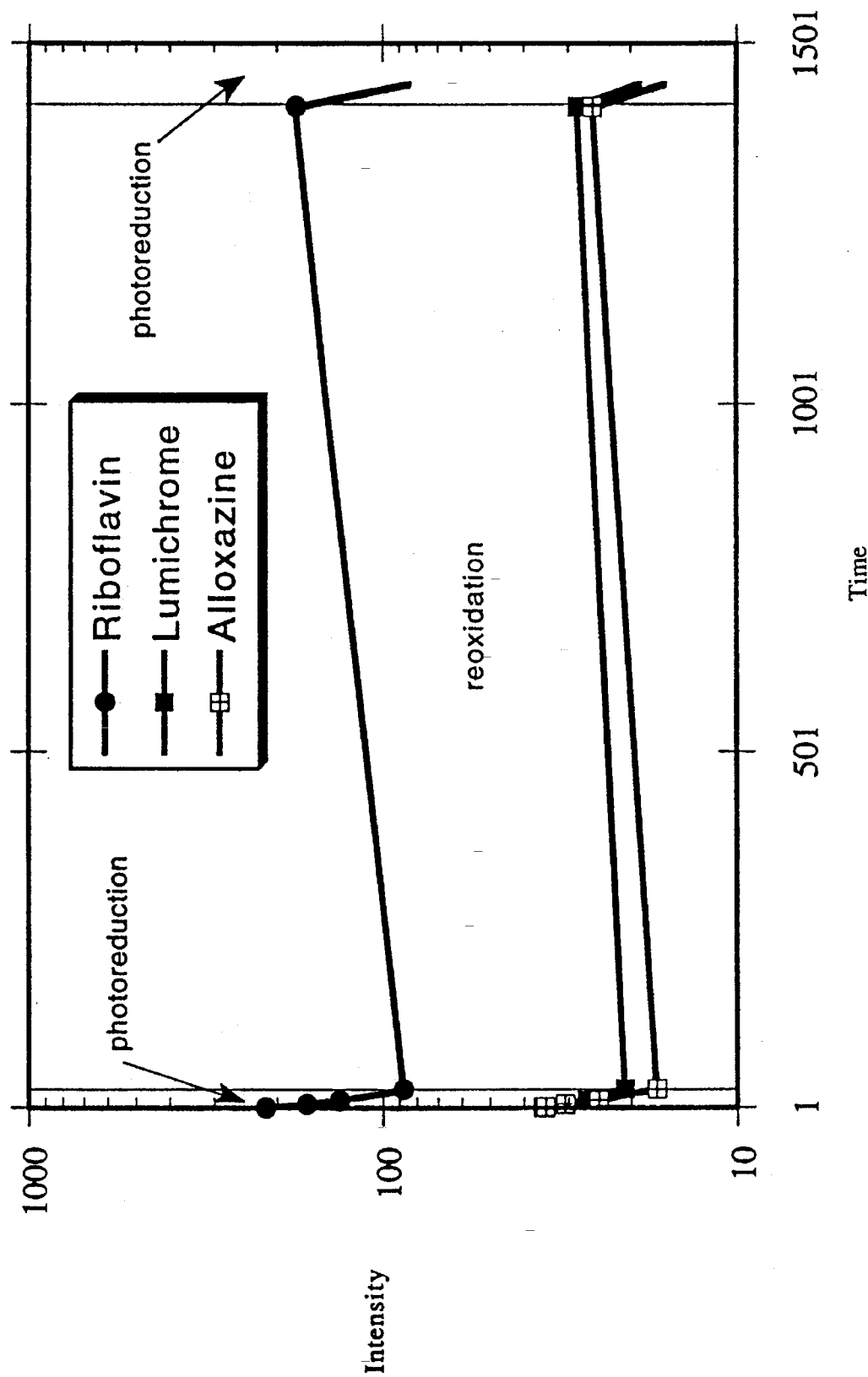
FIG. 10 is a comparison of fluorescent intensity from photoreduction to reoxidation for riboflavin, lumichrome and alloxazine.

Similarly, three additional formulations containing different oxygen indicating dyes were prepared as described above, except that the formulations were modified as described in Table 2. The formulations were incorporated into samples for testing as described above, except that the fluorescence intensity was measured during an initial period of photoreduction under visible light. Then the samples were allowed to reoxidize in the dark for ~24 hours, then were photoreduced under visible light. The results are shown in FIG. 10. Note that all of the formulations oxidize and can be photoreduced. Additionally, glucose can be used as a photoreducing agent. Note also that the filters used on the video imaging system used to acquire the fluorescence data were optimized for the fluorescence emission characteristic of riboflavin, but not alloxazine (benzo[g]pteridine-2,4(1H, 3H)-dione available from Aldrich) and lumichrome. The emission wavelengths of these latter dyes are lower in wavelength, and would be partially filtered out by the 490 nm cut off filters used.

TABLE 2

| Formulation | Thickening Agent Conc. | Indicator Dye Conc. | Photo-Reducing Agent | Buffer |
|---|---|---|---|---|
| Riboflavin | agar, 2% | 0.5 mM riboflavin | 0.36 mM Triethanolamine | pH 6 acetate |

TABLE 2-continued

| Formulation | Thickening Agent Conc. | Indicator Dye Conc. | Photo-Reducing Agent | Buffer |
| --- | --- | --- | --- | --- |
| Lumichrome | agar, 2% | 0.5 mM lumichrome | 3.6 mM Glucose | pH 5 acetate |
| Alloxazine | agar, 2% | 0.5 mM alloxazine | 6 mM Triethanolamine | pH 4 acetate |

EXAMPLE 5

Mixed Dye System

A solution was prepared from 50 mL of pH=8 "Tris" buffer, and 0.75 g of agar with warming. Once the agar had dissolved, 0.280 mL of 1M triethanolamine solution was added along with 0.0064 g (0.017 mmol) of methylene blue and 0.0106 g (0.028 mmol, 1.6 equiv.) of riboflavin. The dark green mixture was stirred for 10 minutes.

The oxygen indicating solution was packaged in a very high oxygen barrier bag (Cryovac® BDF 2001, approximate oxygen transmission rate 5 cc $O_2/m^2$.day.atm available from Cryovac) with essentially no headspace. The mixture formed a solid gel upon cooling. The bag was placed under a fluorescent light to photoreduce. After 20 minutes the color is a pea green. After 1 hour the color is a lime green, and after 2 hours the color is yellow everywhere except around the one small air bubble in the package which is green. After sitting under the lamp overnight the sample is completely reduced. There is no fluorescence or trace of blue color.

The photoreduced sample was stored in the dark to reoxidize. After 4 days the gel is completely fluorescent yellow, but there is no trace of blue (or green color) indicating reoxidation of the riboflavin but not of the methylene blue. The sample was photoreduced a second time in about 2 hours (dissolved oxygen has now been scavenged). After about 1 day, the sample is fluorescent around the seals, but not in the center. After 8 days the sample begins to turn greenish around the seals. Clearly methylene blue oxidizes much more slowly than riboflavin. Riboflavin can be conveniently used to photoreduce methylene blue. And this system could be used to measure higher permeability rates.

EXAMPLE 6

Dye System for Highly Permeable Films

An oxygen transmission indicating system for highly permeable films was prepared by taking 20 mL of a 10% by weight, pH=7 buffered (phosphate), polyethylene oxide (Aldrich, M. W.=100,000) solution in a beaker and adding 0.280 mL of a 1M triethanolamine solution and 0.0068 g (0.018 mM) of methylene blue. After stirring for 5 minutes, 0.0105 g (0.028 mmol) riboflavin was added. The mixture was stirred for 10 minutes at room temperature.

About 10 mL of the dark blue-green solution was placed on a 4 inch square piece of Whatman chromatography paper on a 6 inch square glass plate. The solution was spread around and allowed to soak into the paper. The plate was vacuum packaged in a 3 mil thick polyethylene bag using a Koch model X-200 vacuum package. The plate was then overwrapped with a very high oxygen barrier bag (approximate oxygen transmission rate 20 cc $O_2.m^2$.day.atm) and again vacuum packaged. The package was placed on an $I^2R$™ light table to photoreduce. After 2 hours the plate is fluorescent, but no longer blue. The very high barrier bag overwrap was removed and the plate was stored in the dark to allow reoxidation. After 5 minutes, the plate is a pale blue-green. After 15 minutes the plate is a noticeably darker blue-green. When the overwrap was cut open exposing the plate directly to air, the plate turned dark blue-green within one minute.

EXAMPLE 7

Stability of Polymer-Based Formulations

Five different oxygen indicating formulations were evaluated (Table 3). LOTIS samples were prepared by dip-coating Whatman 3 MM CHR chromatography paper in the oxygen indicating formulation, then placing the coated paper onto a glass plate. The glass plate, together with the coated paper was then vacuum sealed inside of a heavy duty barrier bag (approximate oxygen transmission rate 20 cc $O_2/m^2$.day.atm) available as Cryovac™ B540 barrier bag from Cryovac Division of W. R. Grace & Co. Conn., Duncan, S.C.). The samples prepared by this procedure were then photoreduced periodically for 2 hours on an $I^2R198$ light table, and tested for initial fluorescence intensity immediately after photoreduction and the rate of fluorescence increase after time as described in Example 4.

TABLE 3

| Formulation | Thickening Agent Conc. | Indicator Dye Conc. | Photo-Reducing Agent | Buffer |
| --- | --- | --- | --- | --- |
| Standard Gelatin | gelatin, 7% | 0.5 mM riboflavin | 9 mM $Na_2EDTA$ | None |
| Buffered Gelatin | gelatin, 7% | 0.5 mM riboflavin | 9 mM $Na_2EDTA$ | pH 7 phosphate |
| PvOH | Poly(vinyl alcohol), 10% | 0.5 mM riboflavin | 9 mM Triethanolamine | pH 7 phosphate |
| PEO | Polyox, 10% | 0.5 mM riboflavin | 9 mM Triethanolamine | pH 7 phosphate |
| PAA | Poly(acrylic acid), 10% | 0.5 mM riboflavin | 9 mM Triethanolamine | pH 7 (PAA buffer) |

Figure 11:
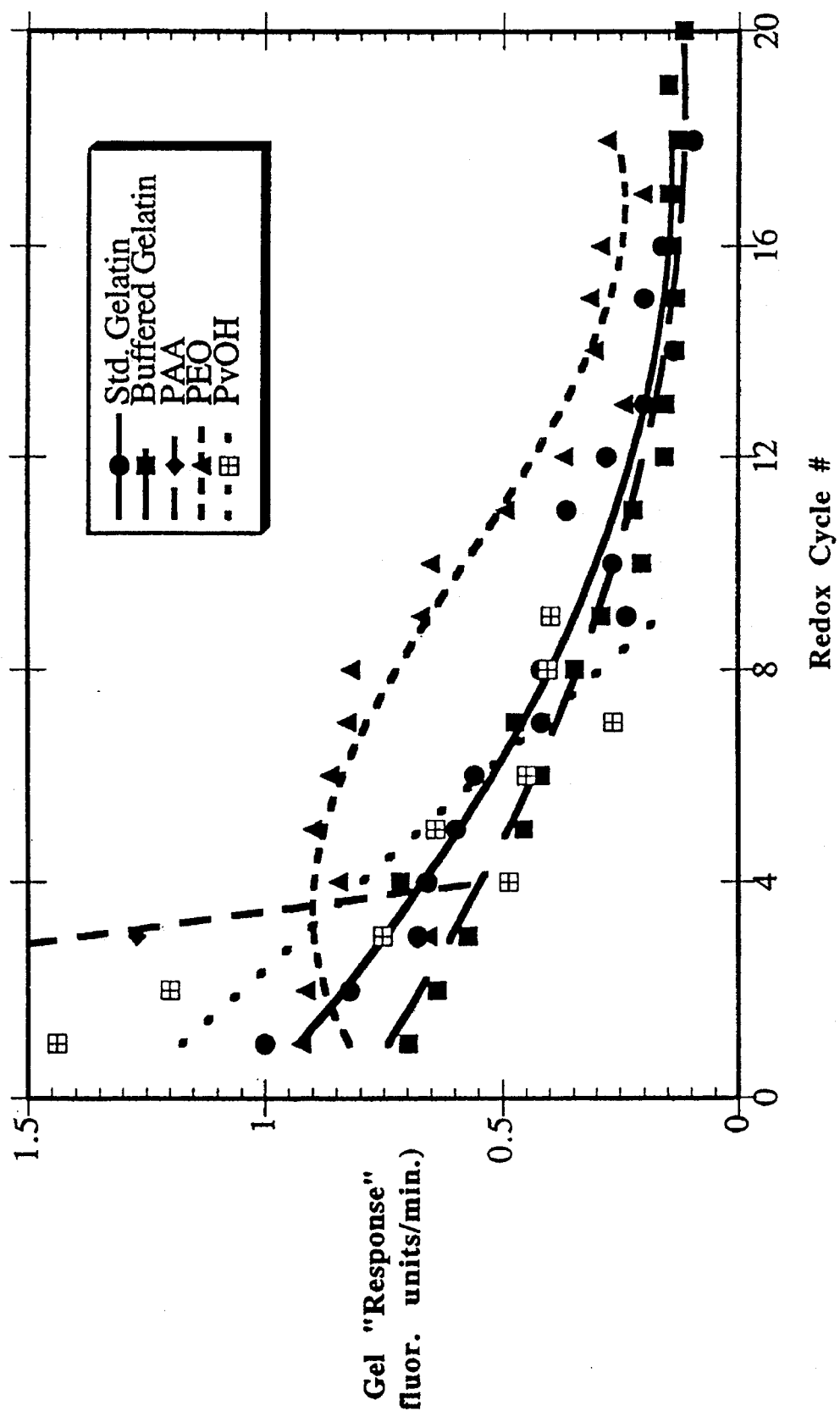
FIGS. 11 and 12 compare change in fluorescent intensity of several different carrier formulations over multiple redox cycles.
Figure 12:
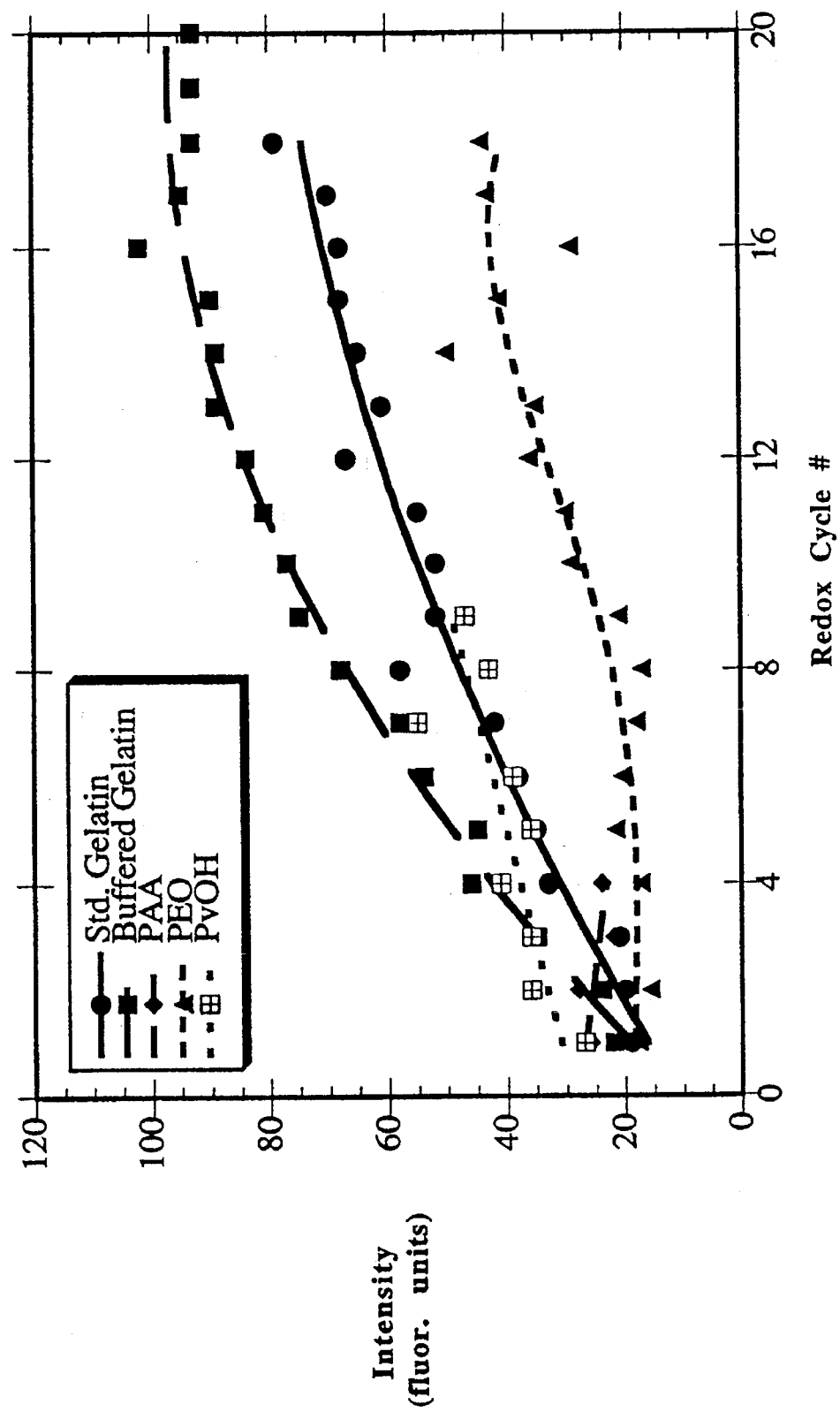

FIG. 11 shows that the "response" of riboflavin gels to oxygen permeation changes as a gel is subjected to repeated redox cycles. For the PAA and PvOH gels, the decrease is so rapid that they no longer function after only 4–5 redox cycles. Both the gelatin and PEO gels continue to "respond" well out to 20 cycles, although there is some loss of sensitivity after about 10 cycles. This drop in response is probably caused by degradation of the riboflavin (oxidative or nucleophilic attach of the flavin structure), or by conversion of riboflavin to lumiflavin or lumichrome derivatives by loss of the ribose group. These latter flavins fluoresce at different wavelengths compared to riboflavin. The response of the PEO gel appears to be better than the standard gelatin formulation, as it remains fairly constant for 8–10 cycles, before dropping to levels typical of the gelatin formulation. In FIG. 12, the trend lines indicate that the photoreduction rates usually decrease—the gels become "harder" to photoreduce—as they are subjected to repeated redox cycles. Changes in the "photoreducibility" or gels also indicate irreversible degradation of the riboflavin dye. The photoreducibility of the PEO gel does not change as rapidly as the gelatin-based gels.

EXAMPLE 8

Easier Sample Preparation of Preferred Polymer-based Formulations

Procedure for preparing the standard gelatin formulation (Table 1): 7 grams of gelatin are added to approximately 93 ml of distilled water. The mixture is heated to boiling briefly, until the gelatin dissolves, then cooled to 35°–40° C. Approximately 188 mg of riboflavin and 303 mg of $Na_2EDTA$ are then added, and the mixture is stirred until the riboflavin and $Na_2EDTA$ are dissolved. Indicating paper is prepared by dipping Whatman 3 MM CHR into the warm solution (35°–40° C.), draining excess solution, then cooling to allow the gelatin to "set".

Procedure for preparing the polymer formulation (PEO, Table 1): 10 grams of polyethylene oxide (e.g., WSR N-10 grade Polyox® are dissolved in approximately 93 g of pH 7 phosphate buffered water. The mixture is heated to boiling briefly, until the PEO dissolves, then cooled to room temperature. Approximately 188 mg of riboflavin and 134 mg of triethanolamine are then added, and the mixture is stirred until the riboflavin and triethanolamine are dissolved. Indicating paper is prepared by dipping Whatman 3 MM CHR into the room temperature solution.

Storage and handling of the PEO solutions is easier because it does not need to be heated before coating the paper, and does not require refrigeration to inhibit mold growth as does the gelatin based formulation.

EXAMPLE 9

Melt Processable polyethylene Oxide Formulations

Figure 13:
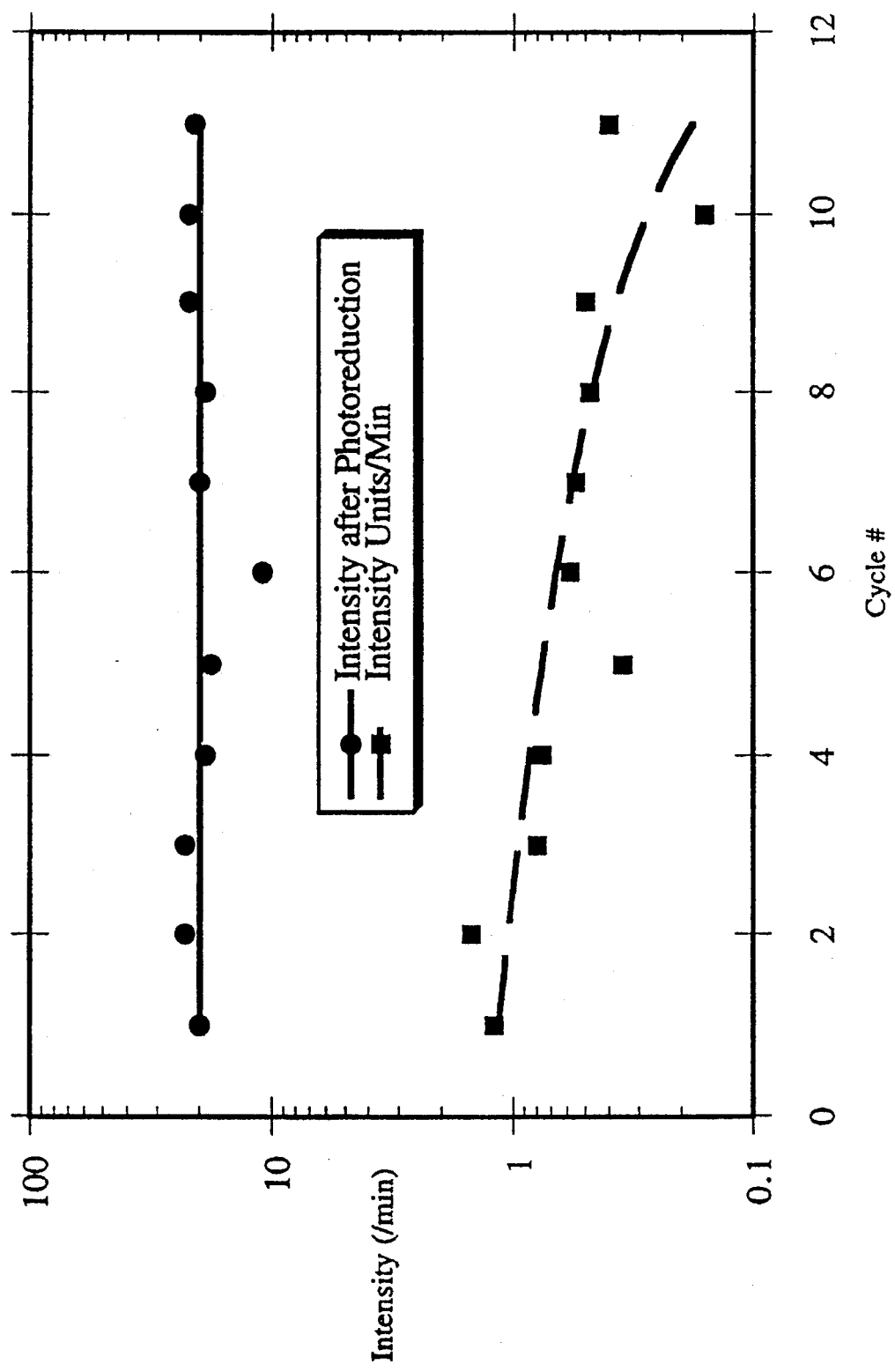
FIGS. 13–15 illustrate change in fluorescent intensity for several melt-processed indicator formulations over multiple redox cycles.

Melt-processable PEO indicator formulations were prepared by melt blending approximately 50 g PEO (high molecular weight polyethylene oxide (WSR N-10 grade POLYOX®)) and 7.5 mg riboflavin in a Brabender mixing chamber at 90° C. for 30 minutes. The mixture was then pressed into a thin film, which was laid on chromatography paper placed on a glass plate, then sprayed with a pH 7 solution of 0.1M triethanolamine. The glass plate containing the wetted PEO/riboflavin film was then vacuum packaged in a heavy duty barrier bag (approximate oxygen transmission rate 20 cc $O_2/m^2$.day.atm). The sample was then tested as described in Example 7, giving the results shown in FIG. 13. FIG. 13 shows that the melt processed Polyox formulation functions substantially like that of the solution coated formulations (e.g., the indicator formulation showed increased fluorescence as oxygen permeated through the covering film and the formulation could be repeatedly photoreduced.

EXAMPLE 10

MELT Processable Acrylic Resin Formulation

Figure 14:
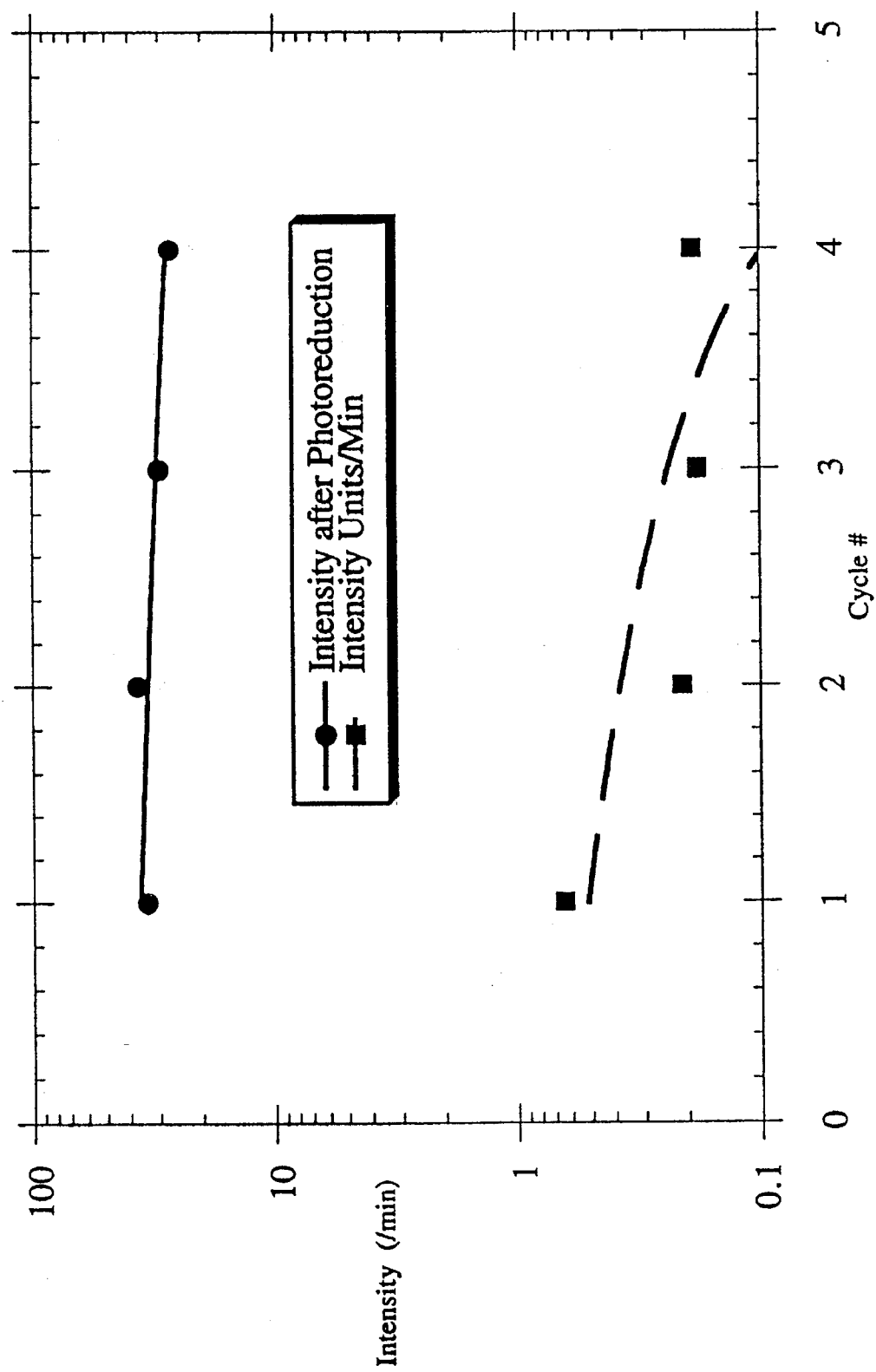

Another melt processable oxygen indicating formulation was prepared as described in Example 9, except that 39 g of an acrylic acid/methacrylic acid copolymer resin (GBC 2580 resin from Belland, Inc., Andover, Mass.) was used instead of PEO. The acrylic resin was melted at 170° C. in a Brabender mixing chamber, then the temperature lowered to 105° C. as 6.88 g of glycerin was added as a processing aid, together with 7.5 mg riboflavin. After compounding, the formulation was pressed into a film and tested as described in Example 9. FIG. 14 shows the test results, indicating that this melt processed formulation functioned substantially like solution coated formulations.

EXAMPLE 11

Melt Processable Polyvinyl Alcohol Formulation

Figure 15:
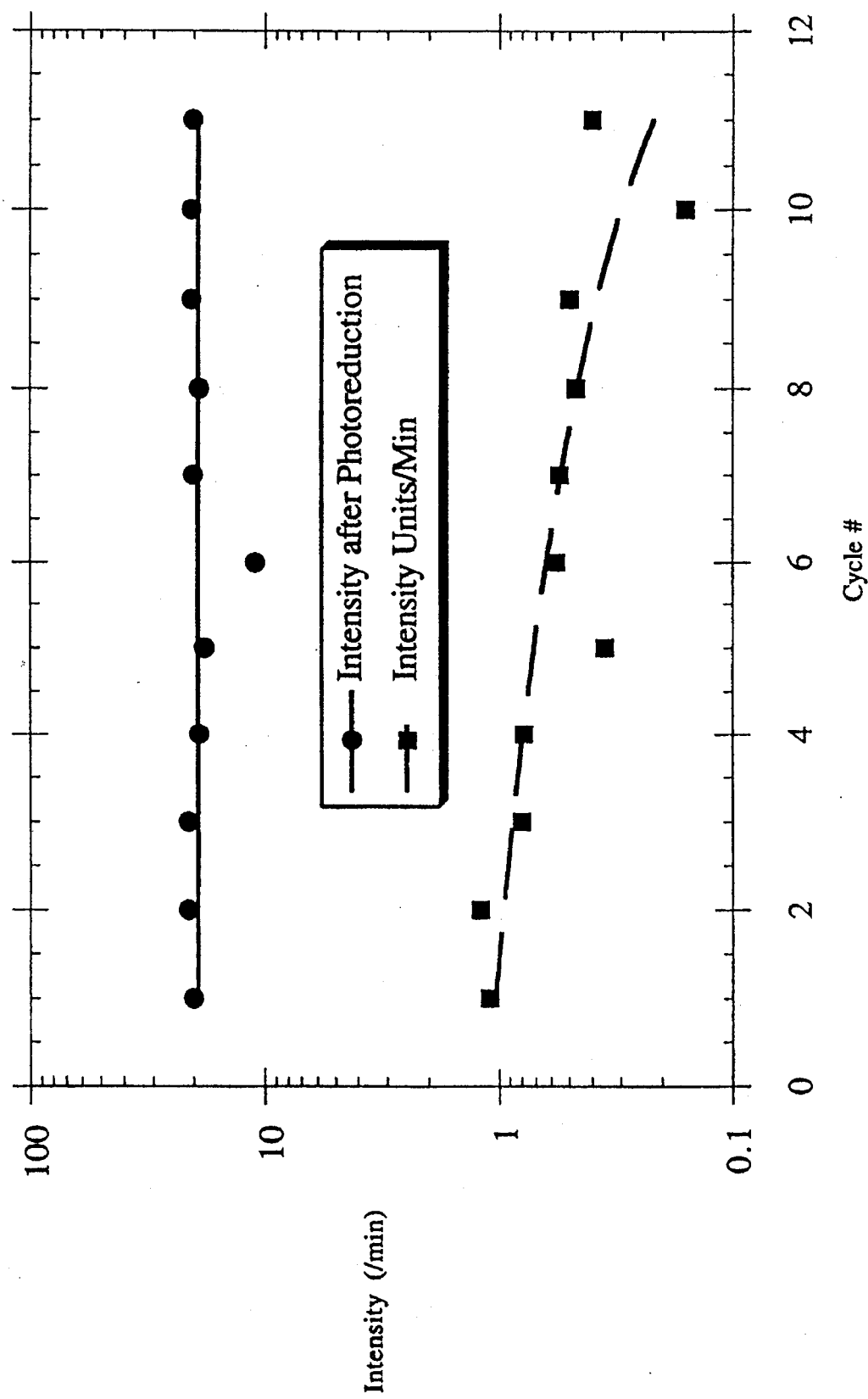

Another melt processable oxygen indicating formulation was prepared as described in Example 9, except that approximately 40 g of a saponified polyvinyl acetate ("PVOH") resin, (Vinex™ resin, available from Air Products and Chemicals, Inc., Allentown, Pa.) was used instead of PEO. The Vinex resin was melt blended in a Brabender mixing chamber together with 7.5 mg riboflavin, and 15% glycerin added as a processing aid. After compounding, the formulation was pressed into a film and tested as described in Example 9. FIG. 15 shows the test results, indicating that this melt processed formulation functioned substantially like solution coated formulations.

What is claimed is:

1. A method of detecting the permeability of an article to oxygen, the steps comprising:

dispersing a redox indicator in a carrier;

extruding the carrier with the redox indicator;

placing the article on the extruded carrier;

photoreducing the redox indicator thereby removing residual oxygen from the extruder carrier and test article;

exposing the article and extruder carrier to oxygen for a period of time;

exposing the redox indicator to light for visualization of redox changes wherein the redox indicator is selected from the group consisting of azines, thiazines, oxazines, flavins, or mixtures thereof, and, wherein the carrier comprises an extrudable, hydrophilic thermoplastic.

2. The method of claim 1, wherein the redox indicator is admixed with a reducing agent, the redox indicator is selected from the group consisting of methylene blue, Celestine Blue, and Nile Blue A, and the reducing agent is a flayin.

3. The method of claim 1 wherein the carrier comprises polymers and copolymers of ethylene oxide, vinyl alcohol, vinyl acetate, acrylic acid and methacrylic acid.

4. The method of claim 3, wherein the carrier comprises polyethylene oxide.

5. The method of any one of claims 1,2, 3 or 4, additionally comprising the step of substantially lowering the initial oxygen content of the carrier and test article by purging with an inert gas or evacuation, or both, before the photoreducing step.

6. A method of detecting the permeability of an article to oxygen, the steps comprising:

dispersing a redox indicator in a carrier;

extruding the carrier with the redox indicator;

placing the extruded carrier on a support;

placing the article adjacent to the extruded carrier and opposite the support wherein the redox indicator is distributed between the test article and the support;

removing residual oxygen from the extruded carrier and test article;

photoreducing the redox indicator;

exposing the article to oxygen for a period of time;

exposing the redox indicator to light for visualization of redox changes to determine the permeability of the article to oxygen, wherein the redox indicator is selected from the group consisting of azines, thiazines, oxazines, flavins, or mixtures thereof, and wherein the carrier comprises an extrudable, hydrophilic thermoplastic.

7. The method of claim 6, wherein the redox indicator is admixed with a reducing agent, the redox indicator is selected from the group consisting of methylene blue, Celestine Blue, and Nile Blue A, and the reducing agent is a flavia.

8. The method of claim 6, wherein the carrier comprises polymers and copolymers of ethylene oxide, vinyl alcohol, vinyl acetate, acrylic acid and methacrylic acid.

9. The method of claim 6, wherein the carrier comprises polyethylene oxide.

* * * * *